US00PP33769P2

(12) United States Plant Patent
Schoone

(10) Patent No.: US PP33,769 P2
(45) Date of Patent: Dec. 21, 2021

(54) ***PHALAENOPSIS* PLANT NAMED 'IMPULSIVE'**

(50) Latin Name: *Phalaenopsis hybrida*
Varietal Denomination: Impulsive

(71) Applicant: FLORICULTURA B.V., Heemskerk (NL)

(72) Inventor: Rene Schoone, Assendelft (NL)

(73) Assignee: FLORICULTURA B.V., Heemskerk (NL)

( * ) Notice: Subject to any disclaimer, the term of this patent is extended or adjusted under 35 U.S.C. 154(b) by 0 days.

(21) Appl. No.: 17/339,961

(22) Filed: Jun. 5, 2021

Related U.S. Application Data

(60) Provisional application No. 62/705,003, filed on Jun. 6, 2020.

(51) Int. Cl.
*A01H 5/02* (2018.01)
*A01H 6/62* (2018.01)

(52) U.S. Cl.
USPC ..... Plt./311
CPC ..... *A01H 6/62* (2018.05)

(58) Field of Classification Search
USPC ..... Plt./311
CPC ..... A01H 6/62
See application file for complete search history.

(56) References Cited

PUBLICATIONS

UPOV hit on *Phalaenopsis* plant named 'Impulsive', QZ PBR 2020/2188, filed Sep. 17, 2020.*

* cited by examiner

*Primary Examiner* — Anne Marie Grunberg
(74) *Attorney, Agent, or Firm* — C. Anne Whealy

(57) ABSTRACT

A new and distinct cultivar of *Phalaenopsis* plant named 'Impulsive', characterized by its upright plant habit; vigorous growth habit; strong flowering stems; strong leaves; freely flowering habit with typically two to three inflorescences per plant, each inflorescence with numerous flowers; large light purple-colored flowers densely covered with variably sized purplish red-colored dots and blotches; and good postproduction longevity.

2 Drawing Sheets

Figure 1:
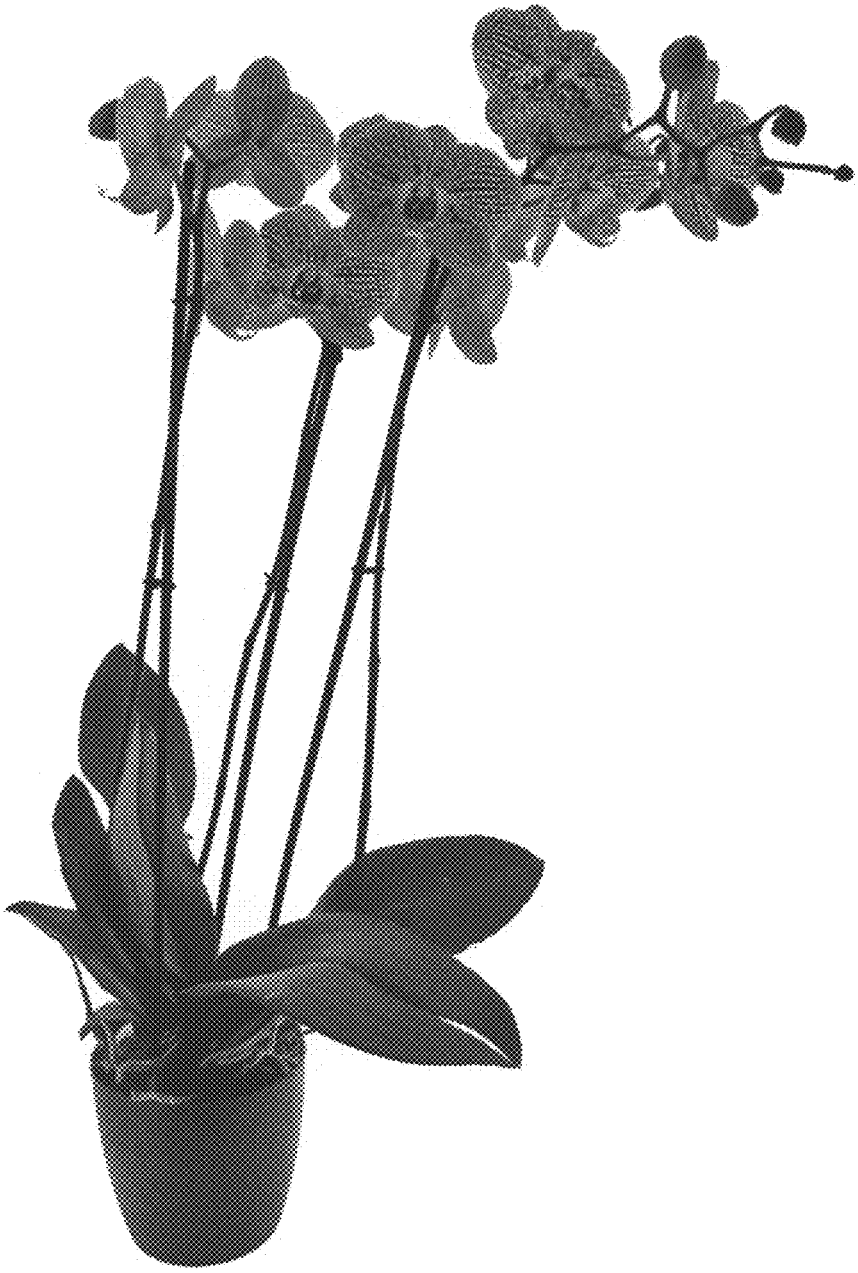

Botanical designation: *Phalaenopsis hybrida.*
Cultivar denomination: 'IMPULSIVE'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Floricultura B.V. of Heemskerk, The Netherlands on Sep. 17, 2020, application number 2020/2188. Foreign priority is not claimed to this European Community Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Phalaenopsis* plant, botanically known as *Phalaenopsis hybrida*, and hereinafter referred to by the name 'Impulsive'.

The new *Phalaenopsis* plant is a product of a planned breeding program conducted by the Inventor in De Lier and Heemskerk, The Netherlands. The objective of the breeding program is to develop new fast-growing and freely flowering *Phalaenopsis* plants with good leaf shape and large flowers with unique and attractive patterns and coloration.

The new *Phalaenopsis* plant originated from a cross-pollination in May, 2014 in De Lier, The Netherlands of a proprietary selection of *Phalaenopsis hybrida* identified as code number B 7039, not patented, as the female, or seed, parent with a proprietary selection of *Phalaenopsis hybrida* identified as code number CX 382, not patented, as the male, or pollen, parent. The new *Phalaenopsis* plant was discovered and selected by the Inventor as a single flowering plant from within the progeny of the stated cross-pollination grown in a controlled greenhouse environment in Heemskerk, The Netherlands in March, 2017.

Asexual reproduction of the new *Phalaenopsis* plant by in vitro meristem propagation in a controlled environment in Assendelft, The Netherlands since March, 2018 has shown that the unique features of this new *Phalaenopsis* plant are stable and reproduced true to type in successive generations.

SUMMARY OF THE INVENTION

Plants of the new *Phalaenopsis* have been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'Impulsive'. These characteristics in combination distinguish 'Impulsive' as a new and distinct *Phalaenopsis* plant:

1. Upright plant habit.
2. Vigorous growth habit.
3. Strong flowering stems.
4. Strong leaves.
5. Freely flowering habit with typically two to three inflorescences per plant, each inflorescence with numerous flowers.
6. Large light purple-colored flowers densely covered with variably sized purplish red-colored dots and blotches.
7. Good postproduction longevity.

Plants of the new *Phalaenopsis* can be compared to plants of the female parent selection. Plants of the new *Phalaenopsis* differ primarily from plants of the female parent selection in flower color as flowers of plants of the new *Phalaenopsis* have more dots and blotches than flowers of plants of the female parent selection. In addition, the curvature of the labellum is stronger in plants of the new *Phalaenopsis* than plants of the female parent selection.

Plants of the new *Phalaenopsis* can be compared to plants of the male parent selection. Plants of the new *Phalaenopsis* differ primarily from plants of the male parent selection in flower color as flowers of plants of the new *Phalaenopsis* have fewer dots and blotches than flowers of plants of the male parent selection. In addition, the ground color of the petals of the new *Phalaenopsis* is light purple whereas the ground color of the petals of the male parent selection is white.

Plants of the new *Phalaenopsis* can be compared to plants of *Phalaenopsis hybrida* 'Cosmopolitan', not patented. In side-by-side comparisons, plants of the new *Phalaenopsis* differ primarily from plants of 'Cosmopolitan' in flower color as flowers of plants of the new *Phalaenopsis* have more dots and blotches, but less dense venation and stripes than flowers of plants of 'Cosmopolitan'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type.

Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'Impulsive' grown in a container.

Figure 2:
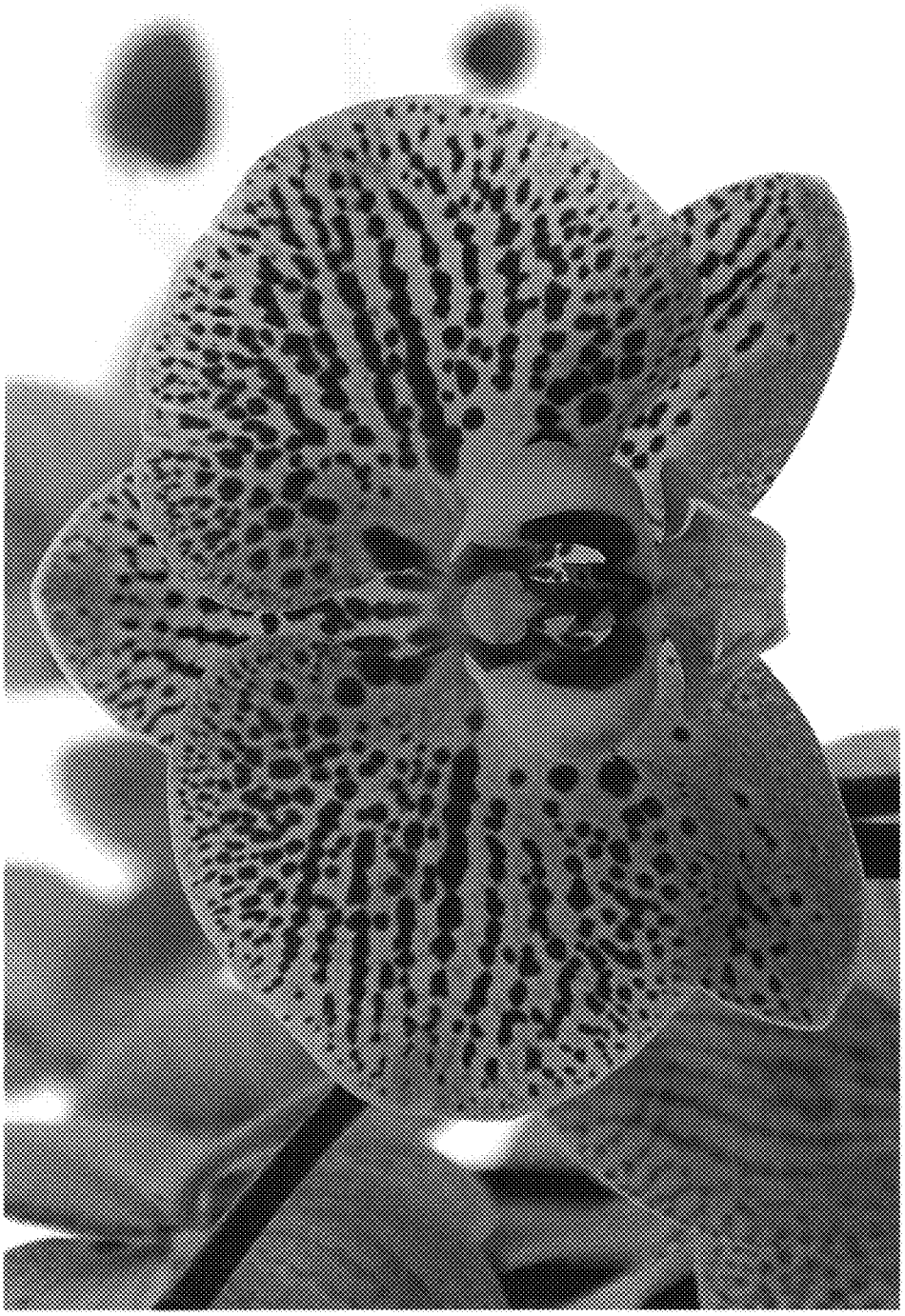

The photograph on the second sheet (FIG. 2) is a close-up view of a typical flower of 'Impulsive'.

DETAILED BOTANICAL DESCRIPTION

The aforementioned photographs and following observations and measurements describe plants grown during the late autumn in 10.5-cm containers in a glass-covered greenhouse in Heemskerk, The Netherlands and under cultural practices typically used in commercial *Phalaenopsis* production. Plants were 18 months old when the photographs and description were taken. During the first twelve months of production of the plants, day and night temperatures averaged 27° C. During the final six months of production of the plants, day temperatures ranged from 20° C. to 22° C. and night temperatures ranged from 18° C. to 20° C. During the 18 months of production, light levels ranged from a minimum of 5,000 lux to a maximum of 10,000 lux. In the following description, color references are made to The Royal Horticultural Society Colour Chart, 2015 Edition, except where general terms of ordinary dictionary significance are used.

Botanical classification: *Phalaenopsis hybrida* 'Impulsive'.

Parentage:

*Female parent.*—Proprietary selection of *Phalaenopsis hybrida* identified as code number B 7039, not patented.

*Male parent.*—Proprietary selection of *Phalaenopsis hybrida* identified as code number CX 382, not patented.

Propagation:

*Type.*—By in vitro meristem propagation.

*Time to initiate roots, summer and winter.*—About two weeks at temperatures about 28° C. to 30° C.

*Time to produce a rooted young plant, summer and winter.*—About 20 to 25 weeks at temperatures about 28° C. to 30° C.

*Root description.*—Thick, fibrous; typically grey to green in color; actual color of the roots is dependent on substrate composition, water quality, fertilizer, substrate temperature and age of roots.

*Rooting habit.*—Low amount of branching; medium density.

Plant description:

*Plant form and growth habit.*—Herbaceous epiphyte; upright plant habit with typically two to three inflorescences per plant, each inflorescence with numerous flowers; monopodial; vigorous growth habit and moderate to rapid growth rate.

*Plant height, substrate level to top of foliar plane.*—About 20.5 cm.

*Plant height, substrate level to top of inflorescences.*—About 62 cm.

*Plant diameter or spread.*—About 38 cm.

Leaf description:

*Arrangement and quantity.*—Distichous, simple; sessile; about six leaves per plant.

*Length.*—About 23.7 cm.

*Width.*—About 8.4 cm.

*Aspect.*—Upright to outwardly arching.

*Shape.*—Elliptic to narrowly oblong and narrowly obovate; slightly concave and slightly carinate.

*Apex.*—Unequal broadly acute.

*Base.*—Sheathing. Sheath length: About 2.2 cm. Sheath width: About 1.6 cm. Sheath color: Close to 143A and 143B.

*Margin.*—Entire; not undulate.

*Texture and luster, upper surface.*—Smooth, glabrous; slightly glossy.

*Texture and luster, lower surface.*—Smooth, glabrous; matte.

*Venation pattern.*—Camptodromous.

*Color.*—Developing leaves, upper surface: Slightly darker than between NN137A and 147A. Developing leaves, lower surface: Close to 146A; towards the margins and midrib, tinged with close to N186C. Fully expanded leaves, upper surface: Close to NN137A; venation, close to between NN137A and 139A. Fully expanded leaves, lower surface: Close to between 146A and 147B; venation, close to 147A.

Inflorescence description:

*Appearance and flowering habit.*—Showy zygomorphic flowers arranged on axillary branched racemes; typically two or three inflorescences per plant; each inflorescence with about ten flowers; flowers face outwardly on arching inflorescences supported by upright peduncles; flowers with three petals, two lateral petals and one center petal transformed into a labellum and three sepals.

*Fragrance.*—None detected.

*Time to flower.*—Plants begin flowering about six months after planting; plants flower naturally during the winter into the spring.

*Flower longevity.*—Long flowering period, individual flowers maintain good substance for about eight weeks on the plant; flowers not persistent.

*Inflorescence length (lowermost flower to inflorescence apex).*—About 32.4 cm.

*Inflorescence width.*—About 16 cm.

*Flower buds.*—Height: About 2.1 cm. Diameter: About 1.4 cm by 1.7 cm. Shape: Broadly ovate. Color: Close to 182B; towards the apex, tinged with close to 184B; towards the base, tinged with close to between 147D and 150D; dots, close to 183A and 183B.

*Flower size.*—Large, about 8.4 cm (vertical) by 9.6 cm (horizontal).

*Flower depth.*—About 3.1 cm.

*Petals, quantity and arrangement.*—Three, two lateral petals and one center petal transformed into a labellum.

*Lateral petals.*—Length: About 4.6 cm. Width: About 5.6 cm. Shape: Reniform. Apex: Rounded. Margin: Entire. Texture and luster, upper and lower surfaces: Smooth, glabrous, velvety; matte. Color: When opening, upper surface: Close to 76B densely covered with variable dots and blotches arranged in roughly radial lines, close to N79C and close to between N79B to 79C; towards the margins and apex, slightly tinged and covered with finer dots, close to N78A and NN78C; towards the base, close to NN155D and at the base (at the column connection), close to N79C. When opening, lower surface: Close to 76B; towards the margins and apex, close to 76C to 76D; blotches from upper surface visible, close to 77B and N79B; venation, lighter than close to N77D. Fully opened, upper surface: Close to 76B and 76C densely covered with variable dots and blotches arranged in roughly radial lines, close to N79C and close to between N79B to 79C; towards the margins and apex, slightly tinged and covered with finer dots, close to N78A, N78B and NN78C; towards the base, close to NN155D and at the base (at the column connection), close to N79B; color does not change with subsequent development. Fully opened, lower surface: Close to 76C; towards the margins and apex, close to 76A; blotches from upper surface visible, close to 77B; venation, lighter than close to N77D; color does not change with subsequent development.

*Labella.*—Appearance: Three-parted with two lateral lobes and a central lobe. Length, lateral lobes: About 2.3 cm. Width, lateral lobes: About 1.5 cm. Length, central lobe: About 3.7 cm. Width, central lobe: About 7 mm to 25 mm. Shape, lateral lobes: Obovate. Shape, central lobe: Deltoid. Apex, lateral lobes: Obtuse. Apex, central lobe: Cleft with two narrow and strongly recurved cirrose tips, about 1.7 cm in length and about 1.6 mm in width. Margins, lateral lobes: Entire; coarsely undulate. Margins, central lobe: Entire. Texture and luster, upper and lower surfaces: Smooth, glabrous, moderately velvety; matte. Callosities: Located at the base of the labellum and attachment point of the lateral petals; about 6 mm in length, about 6 mm in width and about 5 mm in height. Color: When opening, upper surface: Lateral lobes: Close to NN155D; basal margin, close to 10B; at the base, close to 187B and 187C. Central lobe: Close to between 76D and NN155D, widest part, close to 160B to 160C, with fine dots and stripes, close to N78B and N78C; towards the base, close to N79A and at the base, close to 76C; cirrose tips, close to NN155D tinged with close to N78C. Callosities: Close to 4D and 187B. When opening, lower surface: Lateral lobes: Close to NN155C; margins, close to 8B and basal margin, close to 10C; towards the base, close to N77C. Central lobe: Close to 77C flushed with close to 77B; towards the margins, close to 160B; at the base, close to 84D; cirrose tips, close to NN155D tinged with close to N78C. Fully opened, upper surface: Lateral lobes: Close to NN155D; towards the apex, tinged with close to 77C; basal margin, close to 12B; at the base, close to 187B. Central lobe: Close to 76C to 76D, widest part, close to 22B, with fine dots and flushed with close to N78B and N78C; towards the base, close to 76B and at the base, close to N186B; cirrose tips, close to NN155D tinged with close to N78B. Callosities: Close to 4B and N186C. Fully opened, lower surface: Lateral lobes: Close to NN155D; basal margin, close to 12C and flushed with close to 77C; towards the base, close to N77C to N77D. Central lobe: Close to 77B flushed with close to between 77A and 77B; towards the margins, close to 161B; at the base, close to between 84D and 156B; cirrose tips, close to NN155D tinged with close to N78C.

*Sepals.*—Quantity and arrangement: Three, one upper dorsal sepal and two lower lateral sepals. Length, dorsal sepal: About 4.8 cm. Width, dorsal sepal: About 3.3 cm. Length, lateral sepals: About 4.9 cm. Width, lateral sepals: About 3 cm. Shape, dorsal sepal: Broadly elliptic to slightly obovate. Shape, lateral sepals: Ovate. Apex, dorsal sepal: Broadly and bluntly acute. Apex, lateral sepals: Acute. Base, dorsal and lateral sepals: Truncate. Margin, dorsal and lateral sepals: Entire. Texture and luster, dorsal and lateral sepals, upper and lower surfaces: Smooth, glabrous, velvety; matte. Color, dorsal sepal: When opening, upper surface: Close to 76C to 76D densely covered with variable dots and blotches arranged in roughly radial lines, close to N79C and close to between N79B to 79C; towards the margins and apex, slightly tinged with close to N78B and covered with finer dots, close to N78A; towards the base, close to NN155D and at the base (at the column connection), close to N78B. When opening, lower surface: Close to 186C; towards the margins and apex, close to N78C to N78D; blotches from upper surface visible, close to N77B; venation, lighter than close to N77C. Fully opened, upper surface: Close to 76B and 76C densely covered with variable dots and blotches arranged in roughly radial lines, close to N79C and close to between N79B to N79C; towards the margins and apex, slightly tinged and covered with finer dots, close to N78A, N78B and NN78C; towards the base, close to NN155D and at the base (at the column connection), close to N78B; color does not change with subsequent development. Fully opened, lower surface: Close to 77C and 77D; central blotch and towards the base, tinged with a blend of close to 71C and 150C; blotches from upper surface visible, close to 77B; venation, lighter than close to N77D; color does not change with subsequent development. Color, lateral sepals: When opening, upper surface: Close to 155C densely covered with variable dots and blotches arranged in roughly radial lines, close to N79B to N79C; towards the margins and apex, close to 76C to 76D and covered with finer dots, close to N78A and N78B; towards the base, close to NN155D and at the base (at the column connection), close to N79B. When opening, lower surface: Close to N77B; center and towards the base, tinged with close to 195C and 196A; blotches from upper surface visible, close to N77D to lighter than N77D; venation, close to N77B. Fully opened, upper surface: Close to 76B and 76C densely covered with variable dots and blotches arranged in roughly radial lines, close to N79C and close to between N79B to N79C; towards the margins and apex, slightly tinged and covered with finer dots, close to N78A, N78B and NN78C; towards the base, close to NN155D and at the base (at the column connection), close to N79B; color does not change with subsequent development. Fully opened, lower surface: Close to 76C; towards the margins and apex, close to 77C to 77D; towards the base, close to 150D; blotches from upper surface visible, close to 77B; venation, lighter than close to N77D and main vein, strongly tinged with close to 150D; color does not change with subsequent development.

*Peduncles.*—Length: About 69.5 cm. Diameter: About 5 mm. Strength: Strong. Aspect: Upright to outwardly arching. Texture and luster: Smooth, glabrous; matte. Color: Close to between 200A and 203A and tinged with close to N189A; fine dots, close to N148A.

*Pedicels.*—Length: About 4 cm. Diameter: About 3 mm. Strength: Moderately strong. Aspect: About 55° from peduncle axis. Texture and luster: Smooth, glabrous; matte. Color: Close to N148D; proximally, close to 197A to darker than 197A and distally, close to N74D.

*Reproductive organs.*—Androecium: Column length: About 9 mm. Column width: About 6 mm. Column color: Close to 77A to 77B and distally, close to 76B. Pollinia quantity: Two. Pollinia diameter (per two pollinia): About 2.75 mm. Pollinia color: Close to 24A. Gynoecium: Stigma length: About 3 mm. Stigma width: About 4.5 mm. Stigma shape: Reniform. Stigma color: Close to N155A. Ovary length: About 1 cm. Ovary diameter: About 1 mm. Ovary color: Close to NN155D. Seeds and fruits: To date, seed and fruit development have not been observed on plants of the new *Phalaenopsis.*

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate temperatures ranging from about 15° to about 40° C. and are suitable for USDA Hardiness Zones 10 to 12.

It is claimed:

1. A new and distinct *Phalaenopsis* plant named 'Impulsive' as illustrated and described.

* * * * *